Figure 1:
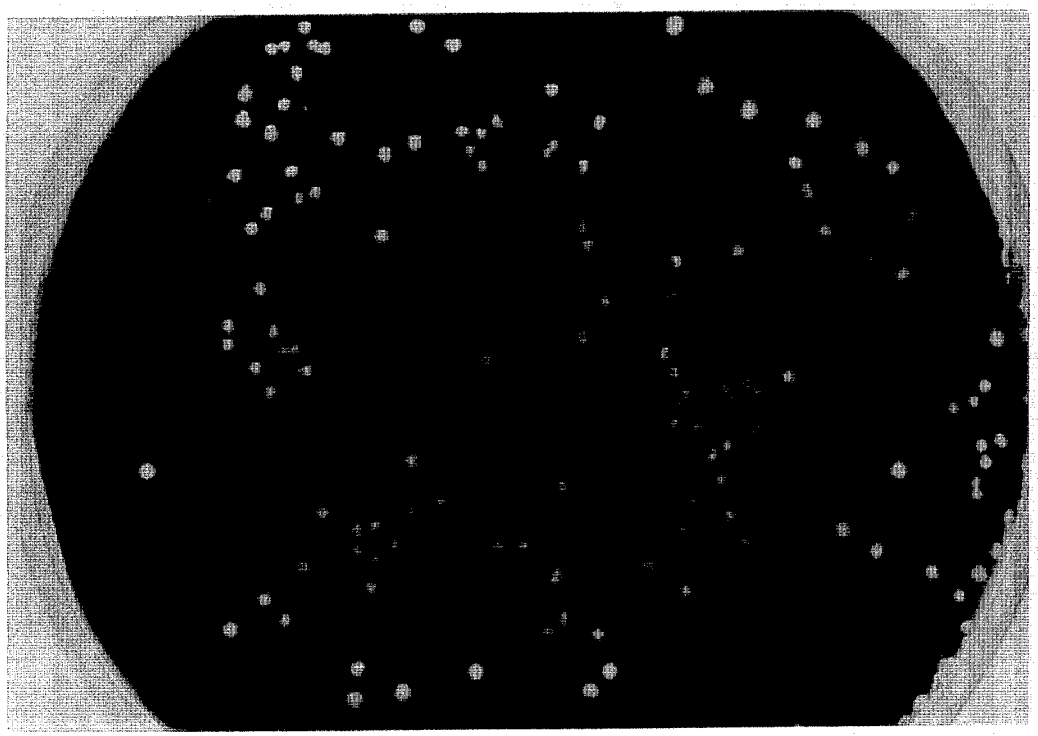

United States Patent [19]

Sandine et al.

[11] Patent Number: 4,528,269
[45] Date of Patent: Jul. 9, 1985

[54] METHOD FOR PRODUCING SINGLE AND/OR MIXED STRAIN CONCENTRATES OF BACTERIA

[75] Inventors: William E. Sandine, Corvallis, Oreg.; Alan R. Huggins, Madison, Wis.

[73] Assignee: The State of Oregon by and through the Oregon State Board of Higher Education on behalf of Oregon State University, Corvallis, Oreg.

[21] Appl. No.: 444,948

[22] Filed: Nov. 29, 1982

Related U.S. Application Data

[63] Continuation of Ser. No. 139,821, Apr. 14, 1980, abandoned.

[51] Int. Cl.³ .................. C12Q 1/04; C12Q 1/70; C12N 1/20; C12R 1/225; C12R 1/23; C12R 1/245; C12R 1/46
[52] U.S. Cl. .................. 435/34; 435/5; 435/253; 435/853; 435/854; 435/856; 435/885; 426/34; 426/43; 426/61; 426/36
[58] Field of Search .................. 435/5, 30, 34, 253, 435/853, 854, 855, 856, 857, 885; 426/34, 36, 41, 43, 61, 231

[56] References Cited

U.S. PATENT DOCUMENTS

| Re. 28,276 | 12/1974 | Farr | 435/885 |
|---|---|---|---|
| 3,041,248 | 6/1962 | Hargrove | 435/885 |
| 3,410,755 | 11/1968 | Etchells et al. | 435/253 |
| 4,038,143 | 7/1977 | Juni | 435/34 |
| 4,218,534 | 8/1980 | La Belle et al. | 435/5 |
| 4,282,255 | 8/1981 | Sandine et al. | 426/7 |
| 4,382,965 | 5/1983 | Sandine et al. | 426/7 |

FOREIGN PATENT DOCUMENTS

651541  9/1937  Fed. Rep. of Germany.

OTHER PUBLICATIONS

Hull, "A Factory Derived Starter Selection Program for Bacteriophage Control Where Single Strain Starters are Used", a paper submitted at the Third Biennial Cheese Industry Conference, Logan, Utah, U.S.A., Aug.-Sep. 1978.

Richardson et al., "Defined Single Strains of Lactic Streptococci in Bulk Culture for Cheddar and Monterey Cheese Manufacture", *J. Dairy Science*, vol. 63, pp. 1981–1986 (1980).

Thomas et al., "Addition of Whey to a Multiple Strain Starter Culture for Casein Making", *New Zealand Journal of Dairy Science and Technology*, vol. 12, pp. 1–4 (1977).

*Difco Manual*, "Simmons Citrate Agar", p. 182, 9th Ed. (1953).

(List continued on next page.)

*Primary Examiner*—Esther M. Kepplinger
*Attorney, Agent, or Firm*—Klarquist, Sparkman, Campbell, Leigh & Whinston

[57] ABSTRACT

An improved method which differentiates or separates heterogeneous populations of fast and slow acid producing strains of bacteria by growth of the strains under closely controlled unique conditions so as to allow the selection of a colony of one or the other strains is described. Preferably a gelled, solid growth medium containing in admixture: (1) milk protein, a milk protein derivative, or a milk protein substitute; (2) an acid, pH sensitive color change indicator; and, (3) a buffering agent is used. The colonies have a contrasting color within and around them because of the effect of the acid produced by the bacteria on the indicator. The growth of the bacteria is under anaerobic or near anaerobic conditions in order to achieve certainty in the colony selection for fast or slow acid production. The bacteria can also be mixed with phage which inhibit or kill the members of a heterogeneous or homogeneous population of bacteria on the medium and grown to produce phage resistant colonies. The relatively large colonies which exhibit enhanced acid production and proteolysis of the milk protein on the plating container are selected for commercial use in preparing fermented products, particularly fermented foods.

21 Claims, 1 Drawing Figure

OTHER PUBLICATIONS

Thomas and Lowrie, "Starters and Bacteriophages in Lactic Acid Casein Manufacture", *Journal of Milk Food Technology*, vol. 38, No. 5, pp. 269-278 (1975).

Czulak et al., "A New Cheese Starter System", *Dairy Industries International*, vol. 44, pp. 17, 18 (1979).

Redys et al., "Detection and Enumeration of Lactic Culture Bacteriophage", *Standard Methods for the Examination of Dairy Products*, 14th Ed., pp. 353, 354 (1978).

Valles, "The Use of Different Oxidation-Reduction Indicators for the Detection of Bacteriophages for Lactic Streptococci", *Le Lait*, vol. 35, pp. 241-258 (1958).

Chr. Hansen's Laboratory, Inc., "Cultures for the Manufacture of Dairy Products", p. 44 (1978).

Brown, J. Howard; and Howe, Paul E., "Transparent Milk as a Bacteriological Medium", *J. Bacteriol.* 7:511-514 (1922).

Olson, H. C., "Preservation of Lactic Cultures", Abstract from *J. Dairy Sci.* 42:388 (1959).

Pearce, L. E.; Skipper, N. A.; and Jarvis, B. D. W., "Proteinase Activity in Slow Lactic Acid-Producing Variants of *Streptococcus Lactis*", *Appl. Microbiol.*, vol. 27, No. 5, pp. 933-937 (May 1974).

Limsowtin et al., New Zealand J. Dairy Sci. Technol., 11: 251-256 (1976).

Fowler et al., Int. Dairy Congress, 3: 1904-1906 (1959).

McKay et al., Applied Microbiol., 23(6): 1090-1096 (1972).

Marshall et al., J. Dairy Res., 43: 449-459 (1976).

Hull, Austral. J. Dairy Technol., 32: 65-66 (1977).

Sozzi et al., Applied Environ. Microbiol., 32(1): 131-137 (1976).

Turner, Nikki; Sandine, W. E.; Elliker, P. R.; and Day, E. A., "Use of Tetrazolium Dyes in an Agar Medium for Differentiation of *Streptococcus lactis* and *Streptococcus cremoris*", *J. Dairy Sci.*, vol. XLVI, No. 5, pp. 380-385 (May 1963).

Barach, Jeffrey T., "Improved Enumeration of Lactic Acid Streptococci on Elliker Agar Containing Phosphate", *Appl. & Environ. Microbiol.*, 38: 173-174 (Jul. 1979).

Rasmussen, Harold L., "Enumeration, Identification of Cultured Product Organisms", (Not Earlier than Jul. 1979).

4,528,269

METHOD FOR PRODUCING SINGLE AND/OR MIXED STRAIN CONCENTRATES OF BACTERIA

This is a continuation of application Ser. No. 139,821 filed Apr. 14, 1980, now abandoned.

BACKGROUND OF THE INVENTION

1. Field of the Invention

The present invention relates to an improved method device for differentiating or separating heterogeneous populations of fast and slow acid producing strains of bacteria to produce single strains or clones. In particular, the present invention relates to a method wherein special growth media and conditions are utilized to achieve the differentiation and wherein the differentiated and selected strains are preferably provided as cultures to producers of fermented products.

2. Prior Art

The principal prior art is described in McKay et al, Applied Microbiology Vol 23, pages 1090–1096 (1972); Limsowtin, G. K. and Terzaghi, B. E. (New Zealand Journal of Dairy Science & Technology Volume 11, pages 65 and 66 (1976)), Limsowtin, G. K., et al New Zealand Journal of Dairy Science Technology 13, pages 1 to 8 (1978), R. J. Marshall et al, Dairy Research, Vol 43, pages 449 to 458 (1976) and in Hull, R. R., The Australian Journal of Dairy Technology pages 65 and 66 (June 1977).

McKay et al describe the problem of the loss of lactose fermenting ability in lactic acid producing cultures in a broth medium. A non-milk agar containing bromocresol purple as an indicator is described for separating colonies which produce acid (yellow) from non-acid producing strains (white) under aerobic conditions. There is no attempt at selection of phase insensitive mutants or recognition of the problem. Thus McKay was studying loss of lactose fermentation and used the non-milk agar medium containing an acid-base indicator to detect non-lactose fermenting (lac−) cells. The selection of lac+ cells on the McKay medium would not be a worth while approach to isolating cells which would yield fast acid producing cultures in milk. Another important determinant for fast acid production in milk is proteolysis (prt). The McKay medium only distinguishes between lac+ and lac− and lac+ prt− and lac+ prt+ cells appear the same on his medium, yet the former would be slow in milk while the latter fast. The problem not solved by McKay et al is to distinguish between lac+ prt− and lac+ prt+ cells, particularly since the large majority of slow acid producing variant cells in milk cultures are lac+ prt−.

Limsowtin et al (1976) described a glycerophosphate buffered, nonfat milk-based, agar medium (GMA) for the differentiation of fast and slow milk coagulating lactic streptococci. Aerobic (air) growth conditions were used for the growth of the bacteria. The medium has been found to be impractical to use since it produced uncertain differentiation of fast and slow acid producing cultures of certain *Streptococcus cremoris* or *Streptococcus lactis* and it was difficult to see white or translucent streptococcal colonies on the white background of this medium. This two strains known to be fast acid producing strains produced colonies which had only a 0.5 mm colony diameter thereby erroneously indicating that they were all slow acid producers. Oblique illumination was used to obtain the published photographs, however visual selection is difficult. Marshall et al describe other phosphate buffered media for the selection process under aerobic conditions where selection is difficult. In selecting starter strains for commercial fermentations, particularly for making fermented dairy products, the method for differentiating and selecting the strains must be completely reliable because of the large volumes of milk or other food being fermented.

Hull describes a method wherein the method of Limsowtin et al can be used by producers of cultures to provide phage resistant, fast acid producing bacterial cultures to producers of fermented dairy products. By this process a portion of the fermented product or a by-product (whey) provides a source for phage which are mixed on the plating medium with the bacteria for differentiation and selection of phage resistant strains. New phage resistant strains are provided to the producers of fermented dairy products and older strains are dropped as phage appear before they have a change to propagate and to vitally infect the older strains. The problem is that the Limsowtin et al method is not reliable or certain enough to make the method suggested by Hull commercially feasible for the culture producers.

OBJECTS

It is therefore an object of the present invention to provide a method wherein heterogeneous populations of fast and slow acid producing strains of bacteria are readily and reproducibly differentiated or separated as to acid producing ability. Further it is an object of the present invention to provide a method wherein phage insensitive strains can be reliably selected. Further still it is an object of the present invention to provide the selected strains as cultures or concentrates of phage insensitive strains of bacteria as a single strain or as a mixture of several such single strains. These and other objects will become increasingly apparent by reference to the following description and to the drawing.

IN THE DRAWING

FIG. 1 is a photograph showing clearly differentiated fast (f) and slow (s) acid producing single strain bacterial colonies produced by the method and plating device of the present invention using an indicator and anaerobic fermentation conditions.

GENERAL DESCRIPTION

The present invention relates to an improved method for the differentiation of heterogeneous populations of fast acid producing strains of a species of bacteria from slow acid producing strains of the same bacteria which comprises providing a gelled, solid bacterial growth medium containing milk protein, a milk protein derivative or a milk protein substitute and containing a pH sensitive indicator which changes color upon contact with acid in the pH range between about 4 and 7 and growing the heterogeneous populations of a strain or strains of acid producing bacteria on the medium to produce single strain acid producing bacterial colonies, wherein the colonies are of varying sizes and have a contrasting color from the growth medium around and within the colonies because of the reaction of the acid in the colonies with the indicator.

A bacterial plating device is used for differentiating and selecting fast acid producing strains of a species of bacteria in a heterogeneous population with slow acid producing strains or variants of the same bacteria. A closed container is used containing a gelled, solid growth medium for the bacteria in admixture with milk protein, a milk protein derivative or a milk protein substitute and a pH sensitive indicator which changes color upon contact with acid in the pH range between about 4 to 7. Preferably anaerobic or near anaerobic conditions are provided in the space.

The method of the present invention produces a concentrate of a single strain or a mixture of single strains of a species of bacteria of the genera Streptococcus or Lactobacillus of the type used for producing lactic acid in foods by fermentation. The selected bacterium is characterized by being a fast acid producer and by having been grown anaerobically on a gelled solid growth medium, wherein preferably the medium includes a pH sensitive indicator which changes color upon contact with acid in the pH range between about 4 and 7, a buffering agent and a milk protein, a milk protein derivative or a milk protein substitute, and by being able to grow in the presence of a phage which kills or impairs the growth of parent strains of the same species to produce the single strains which are then selected and regrown in a second fluid growth medium to produce the concentrates which contains at least about $1 \times 10^6$ cells per ml.

The present invention also relates to the method for selecting phage resistant strains of acid producing bacteria and concentrating the cells for use in producing fermented food products which comprises: growing heterogeneous or homogeneous populations of a strain or strains of the acid producing bacteria anaerobically or nearly anaerobically in the presence of phage on a solid growth medium so as to produce colonies wherein fast acid producing strains produce relatively larger colonies than slow acid producing strains; selecting a large colony; and growing the cells in a fluid growth medium to at least about $10^6$ cells per ml to provide a concentrate of cells.

The present invention particularly relates to the method for providing phage resistant strains of acid producing bacteria to producers of fermented food products which comprises growing heterogeneous or homogeneous populations of a strain or strains of an acid producing bacteria anaerobically or nearly anaerobically in the presence of phage from a sample of the food product or a byproduct of the food product obtained from a producer of the fermented food product on a growth medium which differentiates slow acid producing strains from fast acid producing strains of the bacteria by producing relatively larger colonies of cells of fast acid producing strains in the presence of phage; selecting cells in a large colony having a diameter of at least about 1 mm and growing the cells in the larger colony to at least about $10^6$ cells per ml to provide a culture of cells; and providing the producer which supplied the sample with the culture for use in producing fermented food products.

The method for differentiation and selection produces a concentrate of improved homologous cells of a single strain which is from a clone of a single member of the species and which has the most desirable acid producing properties as well as preferably phage insensitivity. The term "strain" or "variant" as used herein means a member of a single species of bacteria which has a common source or parent with other members and which generally has almost all of the same fermentation characteristics with other members, but which can have a weakness in the ability to produce acid or in the case of milk fermentations have a poor proteolytic ability or have phage sensitivity. A single species of bacteria may have many strains of the same bacterium which differ by one or more fermentation characteristics and thus form a "heterogeneous population". The general fermentation characteristics are determined in relation to sugars and other assimilable carbon sources for the species as listed in Bergey's Manual Eigth Edition (1974). There are commercially available devices for determining fermentation characteristics on sugars and other substrates using microassay techniques. The API series from Analytab Products, Inc., in Carle Place, N.Y. is particularly suitable.

The terms "slow acid producing" and "fast acid producing" are used in the milk fermentation industry in relation to lactic acid producing bacteria. Slow lactic acid producing strains are those which fail to coagulate milk in 18 hours at 21° C. using a 1% by volume inoculum. Fast lactic acid producing strains coagulate milk in less than or equal to 18 hours under the same conditions. The fast acid producing strains develop the relatively larger colonies.

The bacteria are grown so that there are between about 30 and 300 colonies per petri plate or between about 0.5 to 5 per square centimeter of gelled growth medium. Preferably there are less than 100 colonies per plate (about 1.6 per square cm of medium). The reason for these preferred colony densities is that there can be too few or too many colonies on the plate outside of the broad ranges for reliable results. The fast acid producing colonies are at least about 1 mm in diameter.

Many acid indicators can be used in the present invention. The preferred indicator is litmus which changes from blue to red upon contact with acid. Litmus makes proteolysis of the milk protein in the medium by the bacteria readily visible in a ring (p) around the fringes of the fast acid producing colonies (f) as shown in FIG. 1. Milk proteolysis is necessary in most fermentations. Other indicators can be used, such as bromcresol purple (pH range 5.2 to 6.8).

Anaerobic growth conditions provide unexpectedly superior results in terms of the differentiation of fast and slow acid producing colonies. The anaerobic conditions can be provided in the confined space by a vacuum or by providing a reducing or rare gas in the confined space. The preferred gases are nitrogen, hydrogen or other nontoxic gases alone or mixed with carbon dioxide which is assimilated by the lactic acid producing bacteria. Preferably between about 5% and 50% by volume carbon dioxide is used with the balance being hydrogen or nitrogen. Other useful non-oxidizing gases include the rare gases, such as neon and krypton and particularly argon.

An important improvement of the present invention is the use of the acid indicator combined with anaerobic growth conditions which provides a synergistic result in the differentiation and selection and in the homogeneity of the single strain of cells produced. Unexpectedly it has been found that significantly improved differentiation and selection of fast acid producing strains can be achieved with this combination.

The growth medium preferably includes milk protein, a milk protein derivative, preferably nonfat milk or a casein digest, or a milk protein substitute in an amount between about 5 and 15 percent by weight of the gelled solid medium (W/V). Another preferred ingredient is a buffering agent particularly an alkali metal carbonate, phosphate, or an organic sulfonate. The organic sulfonates include alkali metal salts of piperazine-N,N'-bis[2-ethane-sulfonic acid (PIPES), morpholinopropane sulfonic acid (MOPS) and 2(n-morpholino)ethane sulfonic acid (MES)] as described in the abstract of the American Dairy Society Association Meetings June 24 to 27 (1979). Disodium glycerophosphate is preferred. The preferred amount of the buffering agent is between about 0.5 and 5 percent by weight based upon the volume of the gelled solid growth medium (W/V). The agars are preferably Davis TM agar which is produced by the Davis Gelatine Company, Christ Church, New Zealand or Bacto-Agar TM from Difco, Detroit, Mich. Agar substitutes and other gelled solids such as gelatin are also available. Preferably the plating device has a transparent window on the confined space so that the growth of the bacteria can be observed. A conventional petri dish containing the gelled solid growth medium sealed with a confined space around the medium is generally used.

After growth of the bacteria, the relatively large colony is picked from the gelled solid medium and transferred to a second fluid growth medium including assimilable carbohydrate and nitrogen sources and is grown to at least $1 \times 10^6$ cells per ml and preferably to $10^8$ to $10^9$ cells per ml. In this manner, large members of bacterial cells can be produced as a concentrate wherein virtually every individual cell has the same fast acid producing capability. This can be demonstrated by replating the cells on the gelled solid growth medium.

The cells can be held as a concentrated, refrigerated milk culture where milk is the fluid growth medium containing about $1 \times 10^6$ to $1 \times 10^9$ cells per ml or can be concentrated further to above about $1 \times 10^9$ to $1 \times 10^{12}$ cells per ml by removing some of the growth medium. The single strains can be mixed with other single strains produced by the method. The thus concentrated bacteria can be frozen for storage and/or shipment preferably with a freezing stabilizing agent such as glycerol in an amount up to 20 percent by volume or they can be lyophilized. All of these variations in the form of the concentrated bacteria are well known to those skilled in the art.

The bacteria which can be differentiated are preferably species selected from the genera Streptococcus and Lactobacillus and are used for lactic acid production in food products by fermentation. Included are *Streptococcus cremoris, Streptococcus lactis, Streptococcus lactis* subspecies *diacetylactis, Streptococcus thermophilus, Lactobacillus bulgaricus, Lactobacillus acidophilus, Lactobacillus caseii, Lactobacillus lactis,* and *Lactobacillus helveticus.* These are bacteria which are sensitive to phages.

The homologous or heterogeneous phages for the particular strain of bacteria are preferably present when they are grown by the plating method and thus the bacteria produced by the method are thus also phage insensitive. The method can also be repeated using different races of phages when the host bacterium is sensitive to more than one phage. In these ways, cells resistant to more than one phage can be generated.

Phages occur in whey from cheese making. Whey can be used to continuously produce phage insensitive strains by repeated periodic exposure to these phages. Other sources of phage from the producers of fermented products can also be used. This method prevents failures resulting in the loss of hundreds or thousands of gallons of milk in making cultured dairy products where the bacteria are phage sensitive.

SPECIFIC DESCRIPTION

In the following Example 1, the buffering agent was disodium glycerophosphate, the indicator was litmus and anaerobic growth conditions were used.

EXAMPLE 1

The composition of the growth medium, referred to as fast-slow differential agar (FSDA), was as shown in Table 1.

TABLE 1

|  | Grams/liter | Percent by Wt. |
|---|---|---|
| Nonfat milk powder (NFM) | 100 g | 76.9% |
| Davis$_{t.m.}$ agar (New Zealand) | 10 g | 7.7% |
| Disodium glycerophosphate | 19 g | 14.6% |
| Bactolitmus$_{t.m.}$ (litmus) | 1.0 g | 0.8% |
|  |  | 100.0% |

The medium was prepared by dispersing 10 g of Davis agar in 550 ml of double distilled water in a 2 liter flask by steaming for 30 minutes. To the melted agar, 1.0 g of Bactolitmus TM and 19 g disodium glycerophosphate were added and mixed until dissolved. In a separate 1 liter flask, 100 g of the NFM powder was dissolved in 450 ml of double distilled water. The two mixtures were then autoclaved separately for 17 minutes and rapidly cooled to 55° C. in a water bath, combined, and poured into petri plates and flamed to eliminate bubbles as needed. The plates were dried by inverting overnight at room temperature.

Single colony strains were obtained by spreading or streaking a mixture of a heterogeneous population of a specific species of bacteria on the agar and growing the mixture. An atmosphere of hydrogen or hydrogen and carbon dioxide was generated using Gas Pak TM gas generating envelopes (Bio-Quest, Cockeysville, MD) in the confined space over the growth medium in petri plates which were sealed in an air evacuated Gas Pak TM jar. Typical colonies produced within 24 to 36 hours at 30° C. were as shown in FIG. 1, wherein the large fast acid producing colonies (f) were readily distinguishable from the smaller slow acid producing colonies (s). The large colonies (f) measured 1 to 3 mm in diameter and the small colonies (s) between 0.2 to 0.5 mm in diameter or less. The large colonies were selected and had a clear proteolysis ring (p).

It is speculated that the problems encountered by the prior art with aerobic growth of the bacteria on GMA were due to the higher oxygen tension relative to liquid NFM. The effect of anaerobic incubation on colony appearance was remarkable. Not only was excellent colony differentiation achieved, but the incubation period required at 30° C. was about one-half of the time required when incubated under aerobic conditions in air.

Subsequently, 20 different active strains were differentiated and fast acid producing strains selected in the manner of Example 1 including: Sc $A_2$, Sl, $C_2$, Sc $H_2$, Sc HP, Sc 205, Sl c10, Sl $ML_8$, Sc 104, Sc 286, Sc 287, Sc 288, Sc 289A, Sc 289C, Sc 290, Sc 290A, Sc 291, Sc 292, Sc 134, Sc 108 and Sl E where "Sc" represents *Streptococcus cremoris* and "Sl" represents *Streptococcus lactis*. These strains were from the culture collection of Oregon State University, Corvallis, Oreg. and samples are freely available to the public without charge.

All of these species produced fast acid strain colonies (f) within 24 to 36 hours at 30° C. using the improved plating method. Slow acid producing colonies (s) were apparent in different proportions in many strains.

When fast and slow acid producing strains were isolated, cultured separately in NFM for 16 hr, and again plated separately on FSDA using the anaerobic method of the invention, both types yielded all of the same single or homologous colonies produced by the method. Concentrated cultures of fast acid producing strains (f) produced from the selected strains usually were significantly more active in acid production than the parent cultures that consisted of a heterogeneous population of fast and slow strains, which was unexpected. The differentiation and selection of phage resistant strains by the method was also very unexpected.

The following Example 2 describes the differentiation and selection of phage resistant strains.

EXAMPLE 2

Using strains Sc $A_2$, Sc $H_2$, Sl $C_2$ and Sc 104, active phage-insensitive strains were isolated on FSDA when incubated aerobically. These strains were isolated by directly plating the host with an excess of phage by spreading on FSDA as in Example 1. Following 2 to 4 days incubation at 30° C., fast and slow acid producing colonies were apparent. Ten fast acid producing colony strains were picked from each plate and subcultured in NFM as a second fluid growth medium to about $1 \times 10^9$ cells per ml at 21° C. and at 30° C., with and without added phage, and the phage insensitivity was confirmed. Preliminary characterization of the fast acid producing strains indicated that they absorbed phage but without subsequent DNA penetration. Similar variants that absorb phage without subsequent plaque formation were produced as had been reported by Limsowtin et al., N.Z. Jr. Dairy Sci. Technol., 13:1, 1978. The first three strains grew aerobically on GLMA; however this was not true of Sc 104 which had to be grown anaerobically. This demonstrates the reported difficulty that some investigators have had in selecting phage-insensitive mutants that have adequate acid production as described by Limsowtin et al., N.Z. J. Dairy Sci. Technol., 13: 129, 1978.

As phages appeared for fast acid producing strains, isolates of phage-insensitive strains were obtained and used in place of the original phage-sensitive parent strains in Cheddar cheese making. Whey was used as the phage source. Strain Sl $ML_8$ produced by the method was a classic phage-resistant mutant that did not absorb phages, as determined by conventional phage absorption experiments.

The finding of improved colony growth and differentiation using the method of Example 2 was the same for other phage-host combinations. Another alternative is a modification of that reported by Hull, Aust. J. Dairy Technol. 32, 65 (1977) called "Whey Adaptation". This involves culturing the host strain with a whey sample containing phages and then streaking this infected culture and selecting resistant colonies on FSDA. The method of selection and differentiation appeared to be universal for acid producing bacteria.

Example 3 shows the growth of the bacteria under aerobic conditions.

EXAMPLE 3

Example 1 was repeated under aerobic conditions using the FSDA medium. Recognition of typical fast acid producing colonies was either poor or inapparent for 12 (43%) out of 28 single strains incubated aerobically. In general, colony growth was markedly retarded under aerobic incubation for all strains. Consequently, differentiation of fast and slow acid producing colonies was either unreliable or inapparent as all colonies were small (0.5 mm in diameter) and appeared as slow acid producers.

This explains why the method in the original report by Limsowtin and Terzaghi (1976) was unsuccessful in the differentiation of fast and slow colonies. They reported that some fast acid-producing strains gave rise to only slow appearing colonies on glycerophosphate milk agar incubated aerobically. They did not investigate the use of anaerobic incubation to overcome this problem. The problem was that milk-based media such as glycerophosphate milk agar and FSDA would not effectively differentiate the fast and slow colonies because of growth inhibition under aerobic conditions.

There are numerous applications for the improved method and plating device. The most important is the direct selection of phage-insensitive fast acid producing strains. The improved method and plating device can also be used as a tool to directly study various chemicals or conditions influencing the appearance of variants in bacterial strains. Commercially the method is advantageous in the isolation, selection, and screening of fast lactic acid producing starter strains, particularly Cottage and Cheddar cheese and buttermilk producing strains. Thus a Chedder cheese plant in Olympia, Wash. has been on the same culture developed for them for about 1 year, producing about 20,000 pounds of cheese a day or over 5 million pounds. A plant in Tillamook, Oreg. now has over 1200 consecutive 38,000 pound vats (over 4 million pounds of cheese) using a culture developed for their use. The FSD agar is used to isolate phage-resistant fast acid-producing mutants whenever viruses appear for any of the 6 strains in the multiple strain starter cultures. We are convinced that all cheese plants can operate this well when this method is used to keep the cultures active in plants. The cheese is of excellent quality and these cultures eliminate public health problems because of slow vats. The FSD agar facilitates selective manipulation of starter strains which has not been possible previously.

Tests indicate that the addition of optimum amounts (1000 units per petri plate and 0.5% by weight) of catalase and pyruvate, respectively, are substitutes for the anaerobic incubation and addition of ferrous sulfate appears to be effective. These additives degrade the hydrogen peroxide that colonies of lactic Streptococci produce when grown aerobically on milk-based media. This minimizes auto-inhibition of cell growth due to hydrogen peroxide accumulation. However, these additives are not quite as good as anaerobic incubation. Other additives which simulate anaerobic conditions by stimulating the growth of the bacteria under aerobic or anaerobic conditions can be used.

We claim:

1. A method for the differentiation of heterogeneous populations of fast acid producing strains of a species of bacteria from slow acid producing strains of the same bacteria which comprises:
   (a) providing a solid bacterial growth medium containing milk protein, a milk protein derivative or a milk protein substitute and containing a pH sensitive indicator which changes color upon contact with acid in the pH range between about 4 and 7; and (b) growing the heterogeneous populations of a strain or strains of acid producing bacteria substantially anaerobically on the medium to produce single strain acid producing bacterial colonies, wherein the colonies are of varying sizes and have a contrasting color from the growth medium around and within the colonies because of the reaction of the acid in the colonies with the indicator.

2. The method of claim 1 wherein the bacteria are grown in the presence of a phage which can infect the population.

3. The method of claim 2 wherein the bacteria are lactic acid producing and wherein the phage are derived from whey samples from Cottage cheese or cheese making.

4. The method of claim 1 wherein the indicator is selected from the group consisting of litmus, bromcresol purple, bromothymol blue, and mixtures thereof which change color upon contact with acid.

5. The method of claim 1 wherein the bacteria are of the genera Streptococcus or Lactobacillus and are used for lactic acid production in milk by fermentation.

6. The method of claim 5 wherein the bacteria are selected from *Streptococcus cremoris, Streptococcus lactis, Streptococcus lactis* subspecies *diacetylactis, Streptococcus thermophilus, Lactobacillus bulgaricus, Lactobacillus acidophilus, Lactobacillus caseii, Lactobacillus lactis* or *Lactobacillus helveticus.*

7. The method of claim 1 wherein the growth medium contains a buffering agent.

8. A method for the differentiation of heterogeneous populations of fast acid producing strains of a species of bacteria from slow acid producing strains of the same bacteria which comprises:

(a) providing a solid bacterial growth medium containing milk protein, a milk protein derivative or a milk protein substitutes and containing a pH sensitive indicator which changes color upon contact with acid in the pH range between about 4 and 7; and (b) growing the heterogeneous populations of a strain or strains of acid producing bacteria substantially anaerobically in the presence of hydrogen or nitrogen or a mixture of hydrogen or nitrogen and carbon dioxide on the medium to produce single strain acid producing bacterial colonies, wherein the colonies are of varying sizes and have a contrasting appearance and color from the growth medium around and within the colonies because of the reaction of the acid in the colonies with the indicator.

9. The method of claim 8 wherein the growth medium contains an acid buffering agent.

10. The method of claim 9 wherein the acid buffering agent is disodium glycerophosphate.

11. The method for producing phage resistant strains of acid producing bacteria suitable for use in the production of fermented food products, which method comprises:

(a) growing heterogeneous or homogeneous populations of a strain or strains of an acid producing bacteria substantially anaerobically in the presence of phage from a sample of a fermented food product or a by-product of a fermented food product on a solid growth medium which differentiates slow acid producing strains from fast acid producing strains of the bacteria by producing relatively larger colonies of cells of fast acid producing strains in the presence of phage; and (b) selecting cells in a large colony having a diameter of at least about 1 mm and growing the cells in the larger colony to at least about $10^6$ cells per ml to provide a culture of cells suitable for use in producing fermented food products.

12. The method of claim 11 wherein the bacteria area lactic acid producing and wherein the food is a dairy product with whey as the by-product which is a source of the phage.

13. The method of claim 11 wherein the growth medium is a solid growth medium which contains a pH sensitive indicator which changes color upon contact with acid in the pH range between about pH 4 and 7, thereby making the bacteria more readily visible for selection.

14. The method of claim 11 wherein the growth medium contains a buffering agent.

15. The method for producing phage resistant strains of acid producing bacteria suitable for use in the production of fermented food products which method comprises:

(a) growing heterogeneous or homogeneous populations of a strain or strains of an acid producing bacteria substantially anaerobically in the presence of hydrogen, hydrogen and carbon dioxide, nitrogen, or a rare gas and in the presence of phage from a sample of a fermented food product or a by-product of a fermented food product on a solid growth medium which differentiates slow acid producing strains from fast acid producing strains of the bacteria by producing relatively larger colonies of cells of fast acid producing strains in the presence of phage; and (b) selecting cells in a large colony having a diameter of at least about 1 mm and growing the cells in the larger colony to at least about $10^6$ cells per ml to provide a culture of cells suitable for use in producing fermented food products.

16. The method of claim 15 wherein the growth medium contains a buffering agent.

17. The method for selecting phage resistant strains of acid producing bacteria and concentrating the cells for use in producing fermented food products which comprises:

(a) growing heterogeneous or homogeneous populations of a strain or strains of the acid producing bacteria substantially anaerobically in the presence of phage on a solid growth medium so as to produce colonies wherein fast acid producing strains produce relatively larger colonies than slow acid producing strains;

(b) selecting a large colony; and (c) growing the cells in a fluid growth medium to at least about $10^6$ cells per ml to provide a concentrate of cells.

18. The method of claim 17 wherein the solid and the fluid growth media contains milk protein, a milk protein derivative, or a milk protein substitute and agar.

19. The method of claim 17 wherein the growth medium contains a buffering agent.

20. The method for selecting phage resistant strains of acid producing bacteria which comprises:

(a) growing heterogeneous or homogeneous populations of a strain or strains of the acid producing bacteria substantially anaerobically in the presence of the phage on a gelled, solid bacterial growth medium containing milk protein, a milk protein derivative, or a milk substitute and containing a pH sensitive indicator which changes color upon contact with acid in the pH range between about 4 and 7 so as to produce colonies; and (b) selecting a strain which is resistant to the phage.

21. The method of claim 20 wherein the growth medium contains a buffering agent.

* * * * *